United States Patent
Sher et al.

(10) Patent No.: US 6,998,143 B1
(45) Date of Patent: Feb. 14, 2006

(54) FERRIC FORTIFICATION SYSTEM

(75) Inventors: Alexander Sher, Danbury, CT (US); Mark Randolph Jacobson, New Milford, CT (US); Dharam Vir Vadehra, deceased, late of New Milford, CT (US); by Bina Vadehra, legal representative, New Milford, CT (US)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 09/914,637

(22) PCT Filed: Feb. 28, 2000

(86) PCT No.: PCT/EP00/01737

§ 371 (c)(1),
(2), (4) Date: Oct. 23, 2002

(87) PCT Pub. No.: WO00/51446

PCT Pub. Date: Sep. 8, 2000

Related U.S. Application Data

(60) Provisional application No. 60/122,288, filed on Mar. 1, 1999.

(51) Int. Cl.
*A23L 1/304* (2006.01)

(52) U.S. Cl. .......................... 426/74; 426/580; 426/593
(58) Field of Classification Search ................ 426/74, 426/580, 593
See application file for complete search history.

(56) References Cited

U.S. PATENT DOCUMENTS

| 505,896 | A | | 10/1893 | Marfori et al. |
| 3,969,540 | A | | 7/1976 | Jensen |
| 3,992,555 | A | | 11/1976 | Kovacs |
| 4,172,072 | A | | 10/1979 | Ashmead |
| 4,216,144 | A | | 8/1980 | Ashmead |
| 4,303,580 | A | * | 12/1981 | Hidalgo et al. ............. 530/360 |
| H1620 | H | * | 12/1996 | Dolan et al. ................. 426/593 |
| 6,124,258 | A | * | 9/2000 | Sakurai et al. ................. 514/6 |

FOREIGN PATENT DOCUMENTS

| JP | 2-83333 | | 3/1990 |
| JP | 2-83400 | | 3/1990 |
| JP | 9-107917 | | 4/1997 |
| JP | 10-262570 | | 10/1998 |
| JP | 11-75707 | | 3/1999 |
| WO | WO98/42745 | * | 1/1998 |
| WO | WO 98/21953 | * | 5/1998 |

* cited by examiner

*Primary Examiner*—Helen Pratt

(74) *Attorney, Agent, or Firm*—Bell, Boyd & Lloyd LLC

(57) ABSTRACT

An iron fortification complex which may be used to fortify foods and beverages with iron. The complex is formed of ferric ions and caseinate. The complex is sufficiently stable as to be suitable for use in retorted products. However, despite the stability, the iron in the complexes has substantially the same bioavailability as ferrous sulfate.

24 Claims, No Drawings

FERRIC FORTIFICATION SYSTEM

This claims the benefit of Provisional Application Ser. No. 60/122,288 filed on Mar. 1, 1999.

FIELD OF THE INVENTION

This invention relates to a fortification system which may be used to fortify foodstuffs and beverages. The invention also relates to a method of fortifying foodstuffs and beverages.

BACKGROUND OF THE INVENTION

Iron is an essential trace element in animal and human nutrition. It is a component of heme in hemoglobin and of myoglobin, cytochromes and several enzymes. The main role of iron is its participation in the transport, storage and utilization of oxygen. Inadequate iron is a direct cause of the high incidence of anemia, especially among children, adolescents and women. The need for adequate iron is one which extends for the entire life of the human being.

However the body does not produce iron and is totally dependent on an external supply of iron; nutritional or supplementary. The recommended daily allowance for iron intake is usually about 10 mg per day. However the amount needed is dependent on age and sex. Children, women up to the time of menopause, and expectant and nursing mothers have higher requirements of iron.

Therefore iron deficiency is essentially a nutritional problem; a nutritional problem which is common not only in the developing countries. The problem is readily dealt with by consuming foods which naturally provide adequate iron but this is not always possible in disadvantaged societies. Also, many foods normally consumed in developed countries are poor in iron.

To provide a source of iron, many foods and beverages are supplemented with iron. Usually the iron source used in supplementation is a soluble iron salt such as ferrous sulfate, ferrous lactate, ferrous gluconate, ferrous fumarate, ferric citrate, ferric choline citrate, and ferric ammonium citrate. Ferrous sulfate is especially common due to its good bioavailability. Unfortunately, iron supplementation and especially ferrous sulfate supplementation has deleterious effects. In particular, the iron often causes discoloration and off-flavors due to its capacity to interact with polyphenols and lipids and to promote destructive free-radical reactions. This is especially the case at high temperatures and in the presence of oxygen and light.

For example, the addition of a soluble iron source to chocolate milk powder causes the beverage to turn to dark gray when reconstituted with water or milk. It is believed that this is due to the interaction between the iron and iron sensitive ingredients, such as polyphenols. Further, the addition of soluble iron sources to milk, cereals, other fat containing products, mostly products with high level of unsaturated fatty acids, causes flavor changes due to lipid oxidation. Lipid oxidation not only affects the organoleptic properties of foods and beverages, but also undesirably affects the nutritional quality of these products. These interactions can be also enhanced during heat treatment, such as pasteurization or sterilization. In addition, the pH of some iron salts systems may not be compatible with other ingredients or may affect the flavor. Also, from a technical point of view, soluble iron salts can cause corrosion of processing equipment.

Unfortunately, non-soluble or slightly soluble iron sources such as elemental iron, ferric pyrophosphate, etc., are not sufficiently bioavailable.

Therefore, while they may cause little or no discoloration and off-flavor problems, they are poorly absorbed by the body.

To deal with these problems, there have been several attempts to encapsulate or complex soluble iron sources in a way which reduces their reactivity but which maintains their bioavailability. However the attempts have not been entirely successful.

An example of encapsulated iron source is described in U.S. Pat. No. 3,992,555 where iron is coated in an edible, metabolizable fat which has a melting point between about 38° C. and about 121° C. Hydrogenated and refined vegetable oils, and particularly distilled monoglycerides from fully hydrogenated cottonseed oil, are described to be suitable. Although this encapsulation of the iron results in about a 20% reduction in bioavailability, this is stated to be acceptable providing the iron source used has a sufficiently good bioavailability. However, the primary problem is that, if the foods must undergo any form of harsh processing, the capsule is destroyed. Consequently the encapsulated iron cannot be used in products which need to be retorted or subjected to other forms of harsh treatment.

An early example of an iron complex is described in U.S. Pat. No. 505,986. This complex is an iron albumin preparation. The albumin is in intact but heat coagulated form. The complex is recovered as a precipitate. However, when these iron albumin complexes are used in beverages, discoloration and oxidation does occur. For example, chocolate beverages fortified with iron albumin complexes turn a gray color.

More recent examples of iron complexes are described in U.S. Pat. No. 3,969,540 where iron in the ferric form is complexed with hydrolyzed casein or hydrolyzed liver powder. Various other hydrolyzed proteins are also mentioned as possible ligands. The complexes are collected as insoluble precipitates. Unfortunately the iron in the complexes is unlikely to have acceptable bioavailability.

Further examples iron complexes are described in U.S. Pat. No. 4,172,072 where iron is complexed with substantially completely hydrolyzed collagen. Various other completely hydrolyzed proteins are also mentioned as possible ligands. However, the complexes are stated to be stable under acidic conditions and, since the conditions in the gut are acidic, the iron in the complexes is unlikely to have acceptable bioavailability. Also, the complexes are not sufficiently strong to prevent discoloration and lipid oxidation.

Further examples are described in U.S. Pat. No. 4,216,144 where iron in the ferrous form is complexed with hydrolyzed protein; especially soy protein. The bioavailability of the iron in the complexes is claimed to be better than ferrous sulfate. However, when ferrous-soy hydrolysate complexes are used in beverages, discoloration and oxidation does occur. For example, chocolate beverages fortified with ferrous-soy hydrolysate complexes turn a gray color.

Other examples of iron complexes are described in Japanese patent applications 2-083333 and 2-083400. In these applications, ferrous caseinate complexes are used to treat anemia. However, these complexes are not suitable for use in fortifying foods and beverages because they are not sufficiently stable. Also, these complexes are in the form of coagulates and are difficult to disperse.

It is therefore an object of the invention to provide an iron fortification system which is relatively stable but in which the iron is relatively bioavailable.

SUMMARY OF THE INVENTION

Accordingly, in one aspect, this invention provides an iron fortification system suitable for foods and beverages, the fortification system comprising a ferric-caseinate complex.

It has been surprisingly found that ferric-caseinate complexes provide excellent iron fortification systems. The system is stable but the iron is surprisingly bioavailable. Further, the system is made of food grade ingredients and is suitable for use in all foods and beverages.

In a further aspect, this invention provides a foods or beverage which is fortified with iron, the foodstuff or beverage containing an fortification system comprising a ferric-caseinate complex.

The foodstuff or beverage may contain fat. Further, the foods or beverage may contain polyphenols.

In a yet further aspect, this invention provides a process for the preparation of a ferric-caseinate complex, the process comprising:
- dissolving a casein source in an aqueous liquid to provide a casein solution;
- adjusting the pH of the casein solution to about 5.4 to about 6.2;
- dissolving a ferric salt in an aqueous liquid to provide a ferric solution;
- adjusting the pH of the ferric solution to about 5.4 to about 6.2;
- combining the ferric solution with the casein solution and adjusting the pH to about 5.4 to about 7.0; and
- collecting ferric-caseinate complexes which form.

Preferably, the pH of the combined ferric solution and casein solution is adjusted to about 5.8 to about 6.2.

DETAILED DESCRIPTION OF THE PREFERRED EMBODIMENTS

Embodiments of the invention are now described by way of example only. This invention provides an iron fortification system suitable for foods and beverages. The fortification system is a ferric-caseinate complex which is stable but in which the iron remains bioavailable. The resulting iron complexes have reduced ability to cause deleterious effects such as lipid oxidation, color degradation, and vitamin C degradation. This makes the iron complexes an ideal vehicle for fortifying foods and beverages; especially foods and beverages intended to improve nutritional status.

The casein used in the complex may be obtained from any suitable source of substantially intact casein. Examples include sodium caseinate, rennet casein, acid casein, non fat milk solids, and the like. Sodium caseinate obtained from MD Foods Ingredients, Inc under the name MIPRODAN are particularly suitable. The sodium caseinate may be in aqueous or dried form.

The ferric ion may be provided in any suitable, food grade form. Suitable examples include ferric sulfate, ferric chloride, ferric nitrate, ferric citrate, ferric lactate, and ferric fumarate, of mixtures of these ferric salts. Ferric sulfate is particularly preferred.

The complex is produced by combining the ferric ion source and the caseinate source in solution. This must be carried out at a pH selected to avoid precipitation of the caseinate but at which free ferric ions are available. Suitably, the ferric ion source and the caseinate source are combined at a pH in the range of about 5.4 to about 7.0; for example about 5.8 to about 6.2.

The process may be carried out by dissolving a caseinate source in an aqueous liquid such as water; usually under agitation. Mixing is suitably continued until the solution is substantially homogeneous. The pH of the resulting casein solution is adjusted to an acidic pH avoid the formation of ferric hydroxide once the ferric source is added. Preferably, the pH is adjusted to about 5.8 to about 6.0.

The ferric source is also dissolved in an aqueous liquid such as water; usually under agitation. The pH of the ferric solution is maintained at about 5.4 to about 6.2; for example about 5.4 to about 5.6. This may be done by the addition of a suitable base. Any suitable food grade base may be used. Examples of suitable bases include sodium hydroxide, potassium hydroxide, ammonium hydroxide, magnesium hydroxide, sodium carbonate, sodium bicarbonate, potassium carbonate, and potassium bicarbonate. Potassium hydroxide is preferred. The base may be at any suitable strength.

Maintaining the pH of the ferric solution above about 5.4 avoids the pH of the ferric-caseinate mixture dropping to the isoelectric point of casein. In this way, precipitation of the casein may be avoided or at least significantly reduced.

The ferric solution and the caseinate solution are then combined. This is preferably carried out under agitation with the ferric solution added to the caseinate solution; preferably slowly. The amount of the ferric solution which is added may be selected to provide the desired ferric loading. However, it is found that the optimum loading is about 1% by dried weight of iron. Of course, ferric loads of more or less than 1% may be used.

If necessary, the pH of the mixture is then adjusted to maintain it within the range of about 5.4 to about 7.0; preferably about 5.8 to about 6.2 while the ferric-caseinate complexes form. This may be done by adding a suitable food grade acid to the mixture. Examples of suitable acids include phosphoric acid, hydrochloric acid, sulfuric acid, lactic acid, malic acid, fumaric acid, gluconic acid, succinic acid, ascorbic acid, or citric acid. Hydrochloric acid is preferred. The acid may be at any suitable strength.

The ferric-caseinate complexes are then permitted to form under stirring. The time necessary may be anything from about 10 minutes to about 24 hours. Typically the complexes form within about 10 minutes to about 3 hours. If necessary, further acid may be added with time to maintain the pH within the range of about 5.4 to about about 7.0; preferably about 5.8 to about 6.2.

The complexes obtained may be used in liquid form as obtained. If desired, the pH may be adjusted to a neutral pH of about 6.0 to about 7.0 by adding a suitable base. Suitable bases are described above.

More preferably, the complexes are dried to powder. If desired, prior to drying the pH may be adjusted to a pH of about 6.0 to about 8.0 by adding a suitable base. Suitable bases are described above. The drying may be freeze drying or may be spray drying. Any suitable procedure for spray- or freeze-drying the complexes to powder may be used. Suitable procedures are known in the art.

The complexes obtained are insoluble in water but are easily dispersed in water, milk and other liquids.

In use, the complexes are included in the ingredients making up the desired foods or beverage and the ingredients processed in the normal way. Although the bioavailability of the iron may be slightly less than that of ferrous sulfate, it is found that it is well within acceptable limits. In most cases, the statistical difference in bioavailability is not significant. Further, it is found that the complexes are very stable and when used in foods and beverages, do not lead to increased discoloration or off-flavor generation. Moreover, it is found that the complexes do not increase processing problems such as fouling.

The complexes are particularly suitable for use in foods or beverages in liquid form; for example infant formula concentrates and ready-to-drink beverages such as chocolate and malted milk drinks. These foods or beverages usually undergo retorting or other sterilization as part of their processing and hence the ability of the complexes to withstand harsh treatment provides a great improvement. However, the complexes may be used in other types of foods or beverages such as powdered beverages, infant formulas, and infant cereals.

The complexes may also be included in pet foods which usually contain lipids and vitamins.

Products which contain the complexes are perceived to have similar organoleptic properties and color as compared to unfortified products. This offers the advantage that products may be fortified without causing noticeable changes which may adversely affect consumer perception. Also, it is found that vitamin C is not degraded by the complexes. Hence the complexes may be used in products which are intended to be nutritionally balanced.

Specific examples of the invention are now described to further illustrate the invention.

EXAMPLE 1

An amount of 125 g of sodium caseinate (MIPRODAN-30, MD Foods Ingredients, Inc) is dissolved in 2500 g of water under agitation. Mixing is continued until the solution is substantially homogeneous. The pH is adjusted to 5.8 to 6.0 using 5% and 0.1 M HCl solutions.

An amount of 5.483 g of ferric sulfate pentahydrate is dissolved in 500 ml of water at room temperature. The solution is agitated and the pH is carefully adjusted to 5.5 using a 10% NaOH solution followed by a 0.1 M NaOH solution.

The ferric solution is the slowly added to the caseinate solution under vigorous agitation. The suspension is stirred until it is homogeneous; about 1.0 to 1.5 hours. The pH is then adjusted to 6.0 using a 10% NaOH solution followed by a 0.1 M NaOH solution.

The suspension may be used as a liquid fortification system.

EXAMPLE 2

The suspension of example 1 is subjected to freeze drying in a vacuum evaporator. The suspension is frozen to a temperature of −40° C.

The powder may be rapidly suspended in solution.

EXAMPLE 3

The suspension of example 1 is subjected to spray drying in a spinning disk spray drier. The inlet temperature of the drying gas is 145° C. while the outlet temperature is 80° C.

The powder may be rapidly suspended in solution.

EXAMPLE 4

A chocolate powder (QUIK, obtained from Nestle USA, Inc) is dissolved in milk. The chocolate powder constitutes 8.5% by weight of the drink. The chocolate drink is separated into two samples a powder of example 2 or 3 is added to the drinks to provide 12.5 ppm of iron.

The milk is placed in glass jars of 125 ml and heated to 75° C. for 15 seconds. The jars are closed and cooled to room temperature.

The jars are inspected after 1 day, 2 weeks and 4 weeks storage and the drinks evaluated for color and taste. No change in color or flavor is detected as compared to a control which does not contain iron. Also, no coagulation is detected. The results indicate that the complexes are very stable.

EXAMPLE 5

The process of example 4 is repeated except that the milk is autoclaved at 121° C. for 3 minutes.

The jars are inspected after 6 months storage and the drinks evaluated for color and taste. No change in color or flavor is detected. Also, no coagulation is detected. The results indicate that the complexes are very stable.

EXAMPLE 6

The powder of example 3 is added to (i) 22.0 g of chocolate powder (QUIK) and (ii) to 22.0 g of malted beverage powder (MILO—Nestlé Australia Ltd). The powder mixtures are dissolved in 180 ml of boiling water. The beverages are stirred briefly and allowed to stand for 15 minutes. In both cases, the iron fortification is 15 ppm.

The beverages are then judged by a taste panel of five people for color and flavor. In each case, a control beverage produced without the powder of example 3 is used as comparison.

No change is color or flavor is detected.

EXAMPLE 7

The powder of example 3 is added to a chocolate infant cereal to provide 7.5 mg of iron to 100 g of cereal. An amount of 55 g of the cereal is then reconstituted by adding 180 ml of boiling water. The cereal is briefly stirred and allowed to stand for 15 minutes at room temperature.

The cereal is then judged by a taste panel of five people for color and flavor. A control beverage produced without the powder of example 3 is used as comparison.

No change is color or flavor is detected.

EXAMPLE 8

The powder of example 3 is added to chicken fat to provide 40 mg of iron per 1000 g of fat. As a negative control, ferric sulfate is added to chicken fat to provide the same iron loading. Chicken fat without any added iron is used as a positive control.

The fat samples are heated to 100° C. and the lipid oxidation induction time is determined using a Rancimat. No difference in induction time between the fat fortified with the powder of example 3 and the positive control is determined. The induction time of the negative control is 30 to 40% less.

The results indicate that the powder of example 3 does not induce lipid oxidation and is therefore suitable for use in products which contain fats.

EXAMPLE 9

The procedure of example 8 is repeated except that fish oil is used in place of chicken fat. The results are similar.

EXAMPLE 10

The bioavailability of the complexes are determined as follows:—

Animals:—The animals used are weanling male Sprague-Dawley rats aged 3 weeks (IFFA-CREDO, L'Arbresle, France).

Diets:—The control diet is an ICN Low-Iron diet (Soccochim SA, Lausanne, Switzerland) which has an iron content of 3 mg/kg. This diet is casein based and provides for the nutritional requirements of growing rats except for iron.

The experimental diets are:—

Diet A:—The control diet supplemented with $FeSO_4.7H_2O$ to provide 10 mg/kg iron.

Diet B:—The control diet supplemented with $FeSO_4.7H_2O$ to provide 20 mg/kg iron.

Diet 1:—The control diet supplemented with the complex of example 2 to provide 10 mg/kg iron.

Diet 2:—The control diet supplemented with the complex of example 2 to provide 20 mg/kg iron.

Analytical Methods

1) Hemoglobin analysis is performed by anaesthetizing the rats with isoflurane and then drawing a sample of 200 μL of blood from the orbital venous plexus. Blood hemoglobin level in the sample is determined by the cyanmethemoglobin method (Hb kit MPR 3, Bochringer Mannheim GmbH, Germany), using an automated instrument (Hemocue, Baumann-Medical SA, Wetzikon, Switzerland). Commercial quality control blood samples (Dia-HT Kontrollblut, Dia MED, Cressier, Switzerland) having a range of hemoglobin levels are measured with all hemoglobin determinations.

2) Fe-bioavailability as compared to ferrous sulfate heptahydrate is evaluated using a slope-ratio calculation based upon hemoglobin levels. A multiple regression equation relates amounts of iron added to the hemoglobin levels. The equation provides one straight line per diet which intercepts at zero dose. The bioavailability of the iron source relative to ferrous sulfate heptahydrate is then calculated as the ratio of the two slopes. The ratio is multiplied by 100 to provide the relative bioavailability value.

Procedure:—Rats are housed individually in polycarbonate cages, fitted with stainless steel grids. The animals are allowed free access to distilled water. To render the rats anemic, the rats have ad libitum access to the control diet for 24 days. Fresh diet is supplied daily. Spoiling of diet by rats is reduced by covering the diet with a grid.

After 24 days, hemoglobin and weight is determined. Fifty rats with hemoglobin levels between 4.5 and 5.8 mg/dl are randomized into 5 groups of 10 having approximately equal mean hemoglobin and body weight. Each group of animals is fed one of the experimental diets for 14 days. The rats are fed the diets ad libitum beginning with 20 g/day at day 0. The rats have free access to distilled water. Individual food consumption is measured daily. After 14 days, the rats are weighed and hemoglobin is determined.

Results

Mean food consumption and iron intake is not affected by the type of iron source. However the rats receiving no added iron ate less than those receiving iron. The rats consuming diets with 20 mg/kg of added iron consume slightly more than those receiving diets with 10 mg/kg iron.

Weight increase of the rats is not affected by the type of iron source. However, the rats receiving no added iron gained less weight than those receiving iron. The rats receiving diets with 20 mg/kg iron gain slightly more weight than those receiving the diets with 10 mg/kg iron.

The blood hemoglobin levels at the start and at the end of the period are shown in the table below.

| | | Mean hemoglobin values; (Standard Deviation) | | |
|---|---|---|---|---|
| Diet | Added Fe (mg/kg) | Initial hemoglobin (g/dl) | Final hemoglobin (g/dl) | Difference (g/dl) |
| Control | 0 | 5.12 (0.42) | 4.88 (0.43) | −0.24 (0.20) |
| A | 10 | 5.12 (0.41) | 8.66 (0.81) | 3.54 (0.65) |
| B | 20 | 5.12 (0.40) | 11.53 (0.86) | 6.41 (0.82) |
| 1 | 10 | 5.13 (0.39) | 7.77 (0.61) | 2.65 (0.35) |
| 2 | 20 | 5.13 (0.39) | 10.89 (0.79) | 5.76 (0.65) |

The relative bioavailabilities are as follows:—

| Diet | Relative Bioavailability |
|---|---|
| 1, 2 | 87 |
| A, B | 100 |

The bioavailabilities of the Fe-protein complex is similar to that of ferrous sulfate and, from a practical viewpoint, has a very good bioavailability.

The invention claimed is:

1. An iron fortification system in powder form suitable for foods and beverages, the fortification system comprising a ferric-caseinate complex obtainable by:
   dissolving a casein source in an aqueous liquid to provide a casein solution;
   adjusting the pH of the casein solution to about 5.4 to about 6.2;
   dissolving ferric sulfate in an aqueous liquid to provide a ferric solution;
   adjusting the pH of the ferric solution to about 5.4 to about 6.2;
   combining the ferric solution with the casein solution and adjusting the pH to about 5.4 to about 7.0; and
   collecting ferric-caseinate complex.

2. A beverage which is fortified with iron, the beverage containing a fortification system in powder form comprising a ferric-caseinate complex obtainable by:
   dissolving a casein source in an aqueous liquid to provide a casein solution;
   adjusting the pH of the casein solution to about 5.4 to about 6.2;
   dissolving ferric sulfate in an aqueous liquid to provide a ferric solution;
   adjusting the pH of the ferric solution to about 5.4 to about 6.2;
   combining the ferric solution with the casein solution and adjusting the pH to about 5.4 to about 7.0; and
   collecting ferric-caseinate complex.

3. A beverage according to claim 2 which contains a fat.

4. A beverage according to claim 2 which contains polyphenols.

5. A beverage according to claim 4 which includes a chocolate beverage base.

6. A beverage according to claim 4 which is a liquid chocolate drink.

7. A retorted liquid beverage which contains lipid and a stable iron fortification system in powder form comprising a ferric-caseinate complex obtainable by:

dissolving a casein source in an aqueous liquid to provide a casein solution;
adjusting the pH of the casein solution to about 5.4 to about 6.2;
dissolving ferric sulfate in an aqueous liquid to provide a ferric solution;
adjusting the pH of the ferric solution to about 5.4 to about 6.2;
combining the ferric solution with the casein solution and adjusting the pH to about 5.4 to about 7.0; and
collecting ferric-caseinate complex.

8. A retorted liquid beverage according to claim 7, which is a chocolate containing beverage.

9. A retorted liquid beverage which contains polyphenols and a stable iron fortification system in powder form comprising a ferric-caseinate complex obtainable by:
dissolving a casein source in an aqueous liquid to provide a casein solution;
adjusting the pH of the casein solution to about 5.4 to about 6.2;
dissolving ferric sulfate in an aqueous liquid to provide a ferric solution;
adjusting the pH of the ferric solution to about 5.4 to about 6.2;
combining the ferric solution with the casein solution and adjusting the pH to about 5.4 to about 7.0; and
collecting ferric-caseinate complex.

10. The retorted liquid beverage according to claim 9 which is a tea beverage.

11. A beverage powder, which contains lipid and an iron fortification system in powder form comprising a ferric-caseinate complex obtainable by:
dissolving a casein source in an aqueous liquid to provide a casein solution;
adjusting the pH of the casein solution to about 5.4 to about 6.2;
dissolving ferric sulfate in an aqueous liquid to provide a ferric solution;
adjusting the pH of the ferric solution to about 5.4 to about 6.2;
combining the ferric solution with the casein solution and adjusting the pH to about 5.4 to about 7.0; and
collecting ferric-caseinate complex.

12. A beverage powder according to claim 11 which contains chocolate.

13. A process for the preparation of a ferric-caseinate complex, the process comprising:
dissolving a casein source in an aqueous liquid to provide a casein solution;
adjusting the pH of the casein solution to about 5.4 to about 6.2;
dissolving ferric sulfate in an aqueous liquid to provide a ferric solution;
adjusting the pH of the ferric solution to about 5.4 to about 6.2;
combining the ferric solution with the casein solution and adjusting the pH to about 5.4 to about 7.0; and
collecting ferric-caseinate complexes which form.

14. A process according to claim 13 in which the pH of the casein solution is adjusted to about 5.8 to about 6.0.

15. A process according to claim 13 in which the pH of the ferric solution is adjusted to about 5.4 to about 5.6.

16. A process according to claim 13 further comprising neutralizing the ferric-caseinate complexes to a pH in the range of about 6.0 to about 7.0.

17. A process according to claim 13 further comprising drying the ferric-caseinate complexes to powder.

18. A process according to claim 13 in which the pH of the combined ferric solution and casein solution is adjusted to about 5.8 to about 6.2.

19. A food containing a fortification system in powder form comprising a ferric-caseinate complex obtainable by:
dissolving a casein source in an aqueous liquid to provide a casein solution;
adjusting the pH of the casein solution to about 5.4 to about 6.2;
dissolving ferric sulfate in an aqueous liquid to provide a ferric solution;
adjusting the pH of the ferric solution to about 5.4 to about 6.2;
combining the ferric solution with the casein solution and adjusting the pH to about 5.4 to about 7.0; and
collecting ferric-caseinate complex.

20. A food according to claim 19 which contains a fat.

21. A food according to claim 19 which contain polyphenol.

22. A food according to claim 21 which is a chocolate beverage base.

23. A food according to claim 21 which is a liquid chocolate drink.

24. A product in powder form including a ferric-caseinate complex made of food grade ingredients obtainable by:
dissolving a casein source in an aqueous liquid to provide a casein solution;
adjusting the pH of the casein solution to about 5.4 to about 6.2;
dissolving ferric sulfate in an aqueous liquid to provide a ferric solution;
adjusting the pH of the ferric solution to about 5.4 to about 6.2;
combining the ferric solution with the casein solution and adjusting the pH to about 5.4 to about 7.0; and
collecting ferric-caseinate complex.

* * * * *